US005162228A

United States Patent [19]
Sumino et al.

[11] Patent Number: 5,162,228

[45] Date of Patent: Nov. 10, 1992

[54] GYLCERALDEHYDE-3-PHOSPHATE DEHYDROGENASE GENE AND PROMOTER

[75] Inventors: Yasuhiro Sumino, Kobe; Hiroyuki Kimura, Sakai; Masaru Suzuki, Kawanishi, all of Japan

[73] Assignee: Takeda Chemical Industries, Ltd., Osaka, Japan

[21] Appl. No.: 450,253

[22] Filed: Dec. 13, 1989

[30] Foreign Application Priority Data

Dec. 28, 1988 [JP] Japan .................. 63-335238

[51] Int. Cl.[5] .................. C12N 1/15; C12N 15/80; C12N 15/53; C12P 35/00
[52] U.S. Cl. .................. 435/254; 435/320.1; 435/47; 536/27; 935/6; 935/34; 935/68
[58] Field of Search ............ 536/27; 435/172.3, 320.1, 435/254, 47, 925, 926; 935/6, 34, 36, 60, 68

[56] References Cited

U.S. PATENT DOCUMENTS 4,762,786 8/1988 Chapman et al. ................. 435/172.3

FOREIGN PATENT DOCUMENTS 215539 3/1987 European Pat. Off. ..
0281391 9/1988 European Pat. Off. ..
86/06097 10/1986 World Int. Prop. O. ..

OTHER PUBLICATIONS

*ATCC Catalogue of Furgi/Yeasts, 17th edition,* 1987, American Type Culture Collection, Rockville, Md., pp. 4 and 85.
Barredo, J. et al., 1989, *Mol. Gen. Genet.* vol. 216, pp. 91-98.
P. Punt, et al., *Gene,* vol. 69, pp. 49-57 (1988).

Primary Examiner—Richard A. Schwartz
Assistant Examiner—Mary E. Mosher
Attorney, Agent, or Firm—David G. Conlin; Ronald I. Eisenstein

[57] ABSTRACT

A promoter of a glyceraldehyde-3-phosphate dehydrogenase gene of *Acremonium chrysogenum* and a transformant which is obtained by using the expression plasmid containing the promoter and is capable of producing a cephalosporin are disclosed.

9 Claims, 23 Drawing Sheets

Fig. 1

Initiation codon

```
 Sau3AI
GATCAATCAAAATGXXX···XX
    TTAGTTTTACXXX···XXXXXX
```

XXX : Objective gene

Fig. 2

5' -ATGGTTAGAGTTGCTAT (17 mer)

Fig. 5 - 1

```
5' CTGCAGGCGAAAGCCTTTGAAAGTGGCCATCACGACGGTTGTGAATAGAAGAATCGTCA
   10        20        30        40        50        60
   ACAGAAGTGGTGAAGTCATAGCATGGTCATGCCTGTGGCATGCCTGTGTTGGGCCCTGGTGGGA
   70        80        90       100       110       120
   TAGGTACTGTAGATATGTCAATTTCCCAAAAGTAAACGTCCGATACGGCTGTGTAGAGAT
   130       140       150       160       170       180
   CAGAGTGGTTTCTAAGCTGGCGGCTGAGGGATGAGGGACGACGGGCAAGTACGGAATAG
   190       200       210       220       230       240
   AACAGCAAAGAGTATCCGTACCCTCCGTCGATTACTCCCGTCTGTATCCGGATTCAATAC
   250       260       270       280       290       300
   TACTAGTAGGTAATTAAGTACTACCAGAGTAGTAGTTAATCCTGGTACGAGTCGTCG
   310       320       330       340       350       360
   TACATACCAAGCAAGAATTATCTTATAGAAAATATTCCACCTCCACTAACTCTATGCCAACAGCCCGA
   370       380       390       400       410       420
   GGAGGCACAGGCTGATAGAAAATATTCCACCTCCACTAACTCTATGCCAACAGCCCGA
   430       440       450       460       470       480
   CCCTTCGGCTCATGCCGGTACCCGTTGCTGGAGCACTGTGTGGCGCCGTTGTGAGCGACCACCT
   490       500       510       520       530       540
   GGTTAGGTAAGATCAACTGCGTCACTTACTGGAACATCACCGGAAAATGCATGTATTTCC
   550       560       570       580       590       600
```

Fig. 5 - 2

```
         610       620       630       640       650       660
TTCGTACCAGCAGGTTTCGTGAGCGGACGGAAATTTTCGCCCAACACCTGTATGAATAAT
         670       680       690       700       710       720
GCGCCATTTCTTTCCACTTTGGTTTTAGTGGGGGTTCATAATCAAGCCCCGTGTTACCGTG
         730       740       750       760       770       780
ATTCCATGATCAGACGAATGTTGGCAACTACTTTACCTACCAAGTACCTTACGCACCTGG
         790       800       810       820       830       840
CGGAAAGGGCGCGTGAATAAGAGAGCCCTTTCAGCTTCGGCTTCTATCCCCTCCCCCTCC
         850       860       870       880       890       900
CTCCATTCTTCCTTCTTCCATCCACGTCCCCGAGAACCCATCCGTCGTTAACGAA
         910       920       930       940       950       960
AAGCGTCGATTATTATTCCACGAAGCTCACTCTCTTCTTCAAAAAACTACTATAGTAAGTGA
         970       980       990      1000      1010      1020
AGTGCCCTGCTCACGTTCGTCTTGCCTTTGAGCTCTTCCGGCAGCCCCGAGCTCCGGGG
         1030      1040      1050      1060      1070      1080
GAAAGCTCTGAGCTTCCCCCCTCGCCCCTCCTCCAAAACCTTCCCACCCAACCCTCAGCTCA
         1090      1100      1110      1120      1130      1140
CCTCGTCCCATTCTCTCGGCGTCCCTCGGGCGGCCAGATGACTTAGCTGTTGCTTCT
         1150      1160      1170      1180      1190      1200
ACTGCTTCTGCTATTGCTGCTTTTGAATTCTCCGGTCACGCACTCCCCGCATCATCG
```

Fig. 5 - 3

```
         1210      1220      1230      1240      1250      1260
GCTCTCGGCTCTTCGTTAAACTTTTGCTGGCCATGGCTAATAATCTTCCCAGATCAATCA
         1270      1280      1290      1300      1310      1320
AAATGGCCATCAAGGTCGGCATCAACGGGCTTCGGTCGTATTGGACGTATCGTCTTCCGCA
         1330      1340      1350      1360      1370      1380
ACGCCATCGAGCACAGCGACGTCGAGGTCGTTGCTGTGTCAACGACCCCTTCATTGAGACCC
         1390      1400      1410      1420      1430      1440
ACTATGCAGTGAGTTCATCAACATTACCCCTCCATAACCTCTGCATTTTTTTCCCGCTGC
         1450      1460      1470      1480      1490      1500
CCCTCCATTGGCATGATATCATGCGCCACCGGCCGTATCCCGAAATCGGGGCCAGTCCCT
         1510      1520      1530      1540      1550      1560
GCCCATTCTGACCACTCACCACCACCACGACAATATTCGCGCGCGGCGATATATTTCGCAT
         1570      1580      1590      1600      1610      1620
CTCATGGGGTGAAACATAGCAATTGGCTGACACGACGTATCGAAGGCCTACATGCTCAAG
         1630      1640      1650      1660      1670      1680
TATGACTCCTCCCACGGTCTCTTCAAGGGCGACATCTCCCCTGGACGGCAGCGACCTGTCC
         1690      1700      1710      1720      1730      1740
GTGAACGGCAAGAAGGTCAAGTTCTACACTGAGCGCGACCCCGCCAACATCCCCTGGAAG
         1750      1760      1770      1780      1790      1800
GACACTGGCGCCGAGTACATCATCGAGTCCACTGGCGTCTTCACCACCGAGAAGGCC
```

Fig. 5 - 4

```
    1810      1820      1830      1840      1850      1860
AAGGCCCACCTTAATGGTGGGCGGCCAAGAAGGTCATCATCTCTGCTCCCTCCGCCGATGCC
    1870      1880      1890      1900      1910      1920
CCCATGTACGTGATGGGCGTCAACGAGAACACCTACGATGGCAAGGCCGATGTCATCTCC
    1930      1940      1950      1960      1970      1980
AACGCTTCTTGCACCACCAACTGCCTGGCTCCCCTGGCCAAGGTCCTCCACGACAAGTTC
    1990      2000      2010      2020      2030      2040
GGCATCGTCGAGGGTCTCATGACCACCATCCACTCGTACACCTGCCACCCAGAAGACCGTC
    2050      2060      2070      2080      2090      2100
GATGGACCTTCCGCCAAGGACTGGGCGGTGGCCGTGGTGCTGCCCAGAACATCATTCCC
    2110      2120      2130      2140      2150      2160
AGCAGCACCGGGCGCCAAGGCCGTCGGCAAGGTCATCCCCGACCTCAACGGCAAGCTC
    2170      2180      2190      2200      2210      2220
ACTGGCATGTCCATGCGCGTGCCAACTGCCAACGTCTCCGTCGTTGACCTTGACCGCCGGC
    2230      2240      2250      2260      2270      2280
CTCAACAAGGGAGCCAACTACGAGCAGATCAAGGCTGCCATGAAGGAGGCCGCTGCCGGT
    2290      2300      2310      2320      2330      2340
CCCCTTAAGGGTAAGCAATTTGCCCCGAGTACAGGCACTTACGCAGAACGAAACAACTA
    2350      2360      2370      2380      2390      2400
ACAACGCACTCGCAGGCATTCTCGACTACACCGAGGACGAGGTTGTCTCCACCGACCTGA
```

Fig. 5 - 5

```
      2410      2420      2430      2440      2450      2460
ACGGCAACAGCCACTCCTCCTCCATCTTCGACGCCAAGGCCGGTATCTCCCTCAACGACAACT
      2470      2480      2490      2500      2510      2520
TCGTCAAGGTAGTCGCCTGGTACGACAACGAGTGGGGCTACTCCGGTCGTGTCCTCGACC
      2530      2540      2550      2560      2570      2580
TTGTCTCCTACATCTCCAAGGTCGATGCCGGCAAATAAAAAGCGTCCGGCTGTATAGCCA
      2590      2600      2610      2620      2630      2640
CTGTGCTACAGCCACGACGCGGGGGTGCAGATTGTCTTCTGCGATAAATGGATGGCAATC
      2650      2660      2670      2680      2690      2700
ACGACGCTGTCGTCATCTTGATGTGGGTTAGAACAGTAAAAATCACCGGCCCCCGGTAGCC
      2710      2720      2730      2740      2750      2760
AGAGTCAAGTGTCAGCTCAAAGACAAAATTGATCATATTCTGTCGTCAAGCATCATGTGC
      2770      2780      2790      2800      2810      2820
TTACAATTGCCCTGCGATGCGCCGGCATGTAATTCGTTATTTGAACCGCAATGACC
      2830      2840      2850      2860      2870      2880
TTGCAGCTCAAGTGTGAACGAATGAGAGCGTTTAGGTCGAAGGTCCTGCCATAGAAGCCTT
      2890      2900      2910      2920      2930      2940
ACTAACTCCAATCAGACAGAGCGTTTAGGTCGAAGGTCCTGCCGATACCTGCGTGT
      2950      2960      2970      2980      2990      3000
CTCTTGCGAGTCGCTGCGGTCCCCGGTCTGGACACGCCAGCTTGAGCTGGGTCTTGCCACCTCCTGCAAGCTC
      3010      3020      3030      3040      3050      3060
CAAGTCGTCCCCGGTCTGGACACGCCAGCTTGAGCTGGGTCTTGCCACAGAAGTACAGGG
      3070      3080      3090      3100      3110      3120
TCCTAAGTCCCAAGTACGTGACAGTTGGGATAGGTACAGAAACCCTGGCTCCGGATTCGC
      3130      3140      3150
TTGCACATGGCCATCCGTCGCCGACGTCTCGAG 3'
```

Fig. 6-1

```
AUG GCC AUC AAG GUC GGC AUC AAC GGC UUC GGU CGU AUU GGA CGU AUC
Met Ala Ile Lys Val Gly Ile Asn Gly Phe Gly Arg Ile Gly Arg Ile

GUC UUC CGC AAC GCC AUC GAG CAC AGC GAC GAG GUC GUU GCU GUC
Val Phe Arg Asn Ala Ile Glu His Ser Asp Val Glu Val Ala Val

AAC GAC CCC UUC AUU GAG CAC ACC UAU GCA AUG CUC AAG UAU
Asn Asp Pro Phe Ile Glu His Thr Tyr Ala Met Leu Lys Tyr

GAC UCC CAC GGU CUC AAG GGC GAC CUG UCC CUG GAC GGC AGC
Asp Ser His Gly Leu Lys Gly Asp Leu Ser Leu Asp Gly Ser

GAC CUG GUC AAC GUG AAG AAG GUC AUC ACU GAG CGC GAC
Asp Leu Val Asn Val Lys Lys Val Ile Thr Glu Arg Asp

CCC GCC AAC AUC CCC UGG GAC ACU GGC GAG UAC AUC AUC GAG
Pro Ala Asn Ile Pro Trp Asp Thr Gly Glu Tyr Ile Ile Glu

UCC ACU AUC UUC GUC ACC ACC GAG AAG GCC CAC CUU AAU
Ser Thr Ile Phe Val Thr Thr Glu Lys Ala His Leu Asn

GGU GGC GCC AAG AAG GUC AUC UCU GCU CCC UCC GCC GAU GCC CCC
Gly Gly Ala Lys Lys Val Ile Ser Ala Pro Ser Ala Asp Ala Pro
```

Fig. 6 - 2

```
AUG UAC GUG AUG GGC GUC AAC GAG AAC ACC UAC GAU GGC AAG GCC GAU
Met Tyr Val Met Gly Val Asn Glu Asn Thr Tyr Asp Gly Lys Ala Asp

GUC AUC UCC AAC GCU UCU UGC ACC ACC AAC UGC ACC CCC CUG GCC
Val Ile Ser Asn Ala Ser Cys Thr Thr Asn Cys Thr Pro Leu Ala

AUG UAC GUG AUG GGC GUC AAC GAG AAC ACC UAC GAU GGC AAG GCC GAU
Met Tyr Val Met Gly Val Asn Glu Asn Thr Tyr Asp Gly Lys Ala Asp

GUC AUC UCC AAC GCU UCU UGC ACC ACC AAC UGC ACC CCC CUG GCC
Val Ile Ser Asn Ala Ser Cys Thr Thr Asn Cys Thr Pro Leu Ala

AAG GUC CUC CAC GAC AAG UUC GGC AUC GAG GGU CUC AUG ACC ACC
Lys Val Leu His Asp Lys Phe Gly Ile Glu Gly Leu Met Thr Thr

AUC CAC UCG UAC ACU GCC ACC CAG AAG ACC GUC GAU GGA CCU UCC GCC
Ile His Ser Tyr Thr Ala Thr Gln Lys Thr Val Asp Gly Pro Ser Ala

AAG GAC UGG CGC GGU GGC CGU GGC GCU GCC AAC AAC CAG AAU AUU CCC AGC
Lys Asp Trp Arg Gly Gly Arg Gly Ala Ala Asn Asn Gln Asn Ile Pro Ser

AGC ACC GGC GCC AAG GCC GUC AAG GGC GUC AAG GUC AUC CCC GAC CUC AAC
Ser Thr Gly Ala Lys Ala Val Lys Gly Val Lys Val Ile Pro Asp Leu Asn
```

Fig. 6 - 3

```
GGC AAG CUC ACU GGC AUG UCC AUG CGC GUG CCC ACU GCC AAC GUC UCC
Gly Lys Leu Thr Gly Met Ser Met Arg Val Pro Thr Ala Asn Val Ser

GUC GUU GAC CUG ACC GCC CGC CUC AAC AAG GGA GCC AAC UAC GAG CAG
Val Val Asp Leu Thr Ala Arg Leu Asn Lys Gly Ala Asn Tyr Glu Gln

AUC AAG GCU GCC AUG AAG GAG GCC GCU GCC GGU CCC CUU AAG GGC AUU
Ile Lys Ala Ala Met Lys Glu Ala Ala Ala Gly Pro Leu Lys Gly Ile

CUC GAC UAC ACC GAG GAC GAG GUU GUC UCC ACC CUG GAC AAC GGC AAC
Leu Asp Tyr Thr Glu Asp Glu Val Val Ser Thr Asp Leu Asn Gly Asn

AGC CAC UCC UCC AUC UUC GAC GCC AAG GCC GGU AUC GGU AUC CUC AAC GAC
Ser His Ser Ser Ile Phe Asp Ala Lys Ala Gly Ile Gly Ile Leu Asn Asp

AAC UUC GUC GUA AAG GUC GCC UGG UAC GAC AAC GAG UGG GGC UAC UCC
Asn Phe Val Val Lys Val Ala Trp Tyr Asp Asn Glu Trp Gly Tyr Ser

GGU CGU GUC CUC GAC CUU GUC UCU UAC AUC UCC AAG GUC GAU GCC GGC
Gly Arg Val Leu Asp Leu Val Ser Tyr Ile Ser Lys Val Asp Ala Gly

AAA UAA
Lys ***
```

Fig. 12

5'-ATGGGTTCCGTTCCAGT (17 mer)

GYLCERALDEHYDE-3-PHOSPHATE DEHYDROGENASE GENE AND PROMOTER

FIELD OF THE INVENTION

The present invention relates to a promoter of glyceraldehyde-3-phosphate dehydrogenase gene (hereinafter, sometimes, referred to as GLD gene) obtained from *Acremonium chrysogenum* and its use.

*Acremonium chrysogenum* which is microbiologically classified into molds is widely used as a producer of cephalosporin C and deacetylcephalosporin C which are useful in the production of various clinically important semisynthetic cephem antibiotics and, therefore, it is an industrially important microorganism. Accordingly, development of a gene manipulation technique applicable to *Acremonium chrysogenum* has been earnestly requested. Thereby, it can be expected to utilize such a technique not only for improvement of productivity of known antibiotics such as cephalosporin C and deacetylcephalosporin C, but also for the production of novel antibiotics and derivatives thereof.

BACKGROUND OF THE INVENTION

Among gene manipulation techniques using molds as host microorganisms, as a transformation method using *Acremonium chrysogenum* as a host microorganism, there has been reported a method for transforming protoplasts with a recombinant DNA cloning vector plasmid having a hygromycin B resistant gene (hygromycin B phosphotransferase gene) as a selective marker [see S. W. Queener et al., Microbiology—1985; American Society for Microbiology, p 468 (1985)]. Further, for the purpose of the more efficient expression of a foreign gene in microbial cells of *Acremonium chrysogenum*, the present applicant has been already filed a patent application directed to an expression vector which utilizes a region containing a promoter and a translation initiation site of β-isopropyl malate dehydrogenase gene cloned from chromosomal DNA of *Acremonium chrysogenum* (Japanese Patent Laid Open Publication No. 80295/1989).

However, for the potent expression of a foreign gene in microbial cells of *Acremonium chrysogenum*, there is a difficulty in the former method due to the use of a promoter and a translation initiation site derived from a yeast. Although the latter method utilizes a promoter and a translation initiation site derived from *Acremonium chrysogenum*, it is yet insufficient for the potent expression of a foreign gene.

The present inventors have cloned DNA containing a gene coding for GLD which is the enzyme involved in glycolytic pathway from chromosomal DNA of *Acremonium chrysogenum* and have analyzed its gene structure. As a result, it has been found that a region containing the promoter and the translation initiation site of GLD gene can be utilized for the construction of a potent expression vector by using *Acremonium chrysogenum* as a host microorganism.

The primary structure of GLD gene of *Saccharomyces cerevisiae* has been already determined [see The Journal of Biological Chemistry, Vol. 254, No. 19, pp 9839–9845 (1979)] and a gene coding for GLD of *Aspergilus nidulans* has been isolated by using a gene coding for GLD of *Saccharomyces cerevisiae* as a probe [see Gene, 69, pp 49–57 (1988)]. However, GLD gene of *Acremonium chrysogenum* and its utilization in a gene manipulation techniques applicable to such a microorganism have not been reported heretofore in the prior art.

OBJECTS OF THE INVENTION

One object of the present invention is to provide a GLD gene promoter of *Acremonium chrysogenum*.

Another object of the present invention is to utilize the GLD gene promoter of *Acremonium chrysogenum* in a gene manipulation technique applicable to such a microorganism.

These objects as well as other objects and advantages of the present invention will be apparent to those skilled in the art from the following description with reference to the accompanying drawings.

BRIEF EXPLANATION OF THE DRAWINGS

FIG. 1 illustrates the general structure of a synthetic double stranded DNA of from Sau3AI site located in upstream from the initiation codon of GLD gene to a suitable restriction cleavage site located in downstream from the initiation codon of an objective gene.

FIG. 2 illustrates the DNA oligomer obtained in Example 1-2) hereinafter.

FIG. 5 (Parts 1-5) illustrates the DNA base sequence of PstI-XhoI fragment of the plasmid pGL 13.

FIG. 6 (Parts 1-3) illustrates the amino acid sequence of GLD derived from Acremonium chrysogenum presumed in Example 3 hereinafter.

FIG. 12 illustrates the DNA oligomer obtained in Example 6 hereinafter.

SUMMARY OF THE INVENTION

Figure 3:
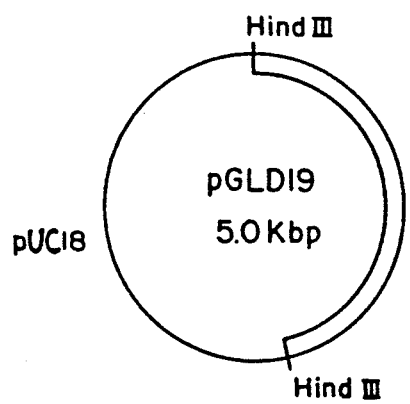
FIG. 3 is the restriction map of the plasmid pGLD obtained in Example 1-5) hereinafter.

The present invention relates to: (1) A DNA fragment having a promoter active part of a glyceraldehyde-3-phosphate dehydrogenase gene of *Acremonium chrysogenum*;

(2) A plasmid incorporated with a glyceraldehyde-3-phosphate dehydrogenase gene promoter of *Acremonium chrysogenum*;

(3) A plasmid of the above (2), wherein a glyceraldehyde-3-phosphate dehydrogenase gene translation initiation site is incorporated in downstream from the glyceraldehyde-3-phosphate dehydrogenase gene promoter site of *Acremonium chrysogenum*;

(4) A plasmid of the above (2) or (3), wherein a structural gene is incorporated in downstream from the promoter or the initiation site;

(5) *Acremonium chrysogenum* transformed with the plasmid of the above (4);

(6) The transformant of the above (5) which is capable of producing a cephalosporin; and (7) A process for producing a cephalosporin which comprises culturing the transformant of the above (6) in a culture medium to produce and accumulate the cephalosporin in the culture and separating the cephalosporin.

DETAILED DESCRIPTION OF THE INVENTION

The promoter active part of GLD gene, the GLD gene translation initiation site and the DNA containing a structural gene coding for GLD, that is, the GLD gene DNA of *Acremonium chrysogenum* according to the present invention can be separated and collected from microbial cells of *Acremonium chrysogenum*.

Examples of *Acremonium chrysogenum* include *Acremonium chrysogenum* ATCC 11550 strain, *Acremonium chrysogenum* ATCC 14553 strain and the like. The DNA coding for GLD gene can be obtained from a chromosomal DNA of *Acremonium chrysogenum*. The chromosomal DNA can be obtained by preparing protoplasts from the microbial cells according to a known method, for example, the method of P. F. Hamlyn et al. [see Enzyme Microbiological Technology, 3, 321 (1981)]or its modification, and preparing the DNA from the protoplasts according to a known method, for example, the method of D. R. Cryer et al. [see Method in Cell Biology, XII, 39 (1975)]or its modification.

As DNA detecting means used for cloning a DNA fragment containing a GLD gene region from the chromosomal DNA, any means which can confirm the existence of GLD gene on the DNA fragment incorporated in a vector plasmid can be employed. For example, there can be employed a method utilizing complementation of a host GLD gene defective strain, a method for detection by hybridization using GLD gene of known yeasts or bacteria or a part thereof labeled with a radio isotope as a probe, and the like. More particularly, GLD gene cloned from *Saccharomyces cerevisiae* IFO 10147 strain according to the report by J. P. Holland et al. [see J. Biol. Chem., 254, 9839 (1979)]can be suitably used as the probe. And, although a host to be used is not specifically limited, usually, *Escherichia coli* is used. A preferred example thereof is the commercially available *Escherichia coli* LE 392 strain (manufactured by STRATAGENE Cloning System Company, U.S.A.). As a vector, there can be used any vector which can be introduced into *Escherichia coli*. Preferably, plasmid vectors such as pBR 322, pUC 18, pUC 19 and the like as well as λphage vector are used. Examples thereof include the commercially available Lambda FIX (manufactured by STRATAGENE Cloning System Company, U.S.A.) and the like.

In order to insert the chromosomal DNA fragment into a vector, the chromosomal DNA can be cleaved or partially cleaved with a suitable restriction enzyme. On the other hand, a vector DNA can be cleaved with the same restriction enzyme as that used for cleavage of the chromosomal DNA or a restriction enzyme which can provide a cleaved site being capable of ligation with the cleaved chromosomal DNA. Then, they can be ligated with a DNA ligase to obtain the desired recombinant DNA wherein the chromosomal DNA fragment is inserted into the vector DNA.

The recombinant DNA can be introduced into a host by a known method. For example, in the case of using a plasmid as a vector, a competent cell method can be employed. In the case of using λphage vector, an in vitro packaging method can be employed. For example, after subjecting Lambda FIX wherein the chromosomal DNA has been incorporated to in vitro packaging by using a commercially available in vitro packaging kit (e.g., Gigapack gold manufactured by STRATAGENE Cloning System Company, U.S.A.), a *Escherichia coli* host can be infected therewith to form plaques. In order to detect a λphage vector containing the objective GLD gene, a plaque hybridization method using the above GLD gene derived from *Saccharomyces cerevisiae* as a probe can be suitably employed. According to a conventional method, λphage is recovered from a plaque wherein hybridization has been observed and the plaque hybridization using the recovered phage is repeated. By repeating this operation several times, λphage vector wherein the chromosomal DNA fragment containing the GLD gene has been inserted can be separated. After separating λDNA from this λphage and then cleaving with a suitable restriction enzyme, it can be subcloned in a vector plasmid. By testing whether the subcloned chromosomal DNA is hybridized with the GLD gene derived from *Saccharomyces cerevisiae* or not, the approximate size and location of the GLD gene can be defined.

These fundamental operations are known and are described in detail in literatures (see Methods in Enzymology, Vol. 68, 1979; Molecular Cloning, 1982).

The base sequence of a DNA coding for GLD gene can be determined by known methods, for example, dideoxy synthetic chain termination method (see Eiichi Soeda et al., "Base Sequence Determination Method for Nucleic Acids", pp 61–113, published by Gakkai Shuppan Center, 1985), Maxam-Gilbert method [see Proceedings of the National Academy of Sciences of the United States of America, 74, 5463 (1977)]or their modifications. The exact location of GLD gene in the DNA base sequence thus determined and the promoter and translation initiation site of GLD gene can be readily defined by analyzing the sequence. In FIG. 5, there is shown the DNA base sequence of GLD gene derived from *Acremonium chrysogenum* ATCC 11550 which is obtained in Example 3 hereinafter. "ATG" from the base No. 1233 is the initiation codon and, in the non-translated region in upstream therefrom, there are "TATTA" (the base Nos. 911 to 915) which are similar to TATA sequence, the sequence in common with promoters of eukaryote [see Proudfoot, Nature, 279, (1979)]. Further, in upstream from the sequence, there are CCATTCT (the base Nos. 842 to 849) which are similar to CAAT sequence, likewise, the sequence in common with promoters of eukaryote [see Breathnach, R and Chembon, P, Annu. Rev. Biochem., 50, (1981]. Thus, the DNA fragment corresponding to the base No.

1 to the initiation codon (the base No. 1233) in FIG. 5 is one example of the DNA fragment containing the promoter and translation initiation site of GLD gene. However, in so far as the function of the promoter is maintained, a part of the DNA fragment from the base No. 1 can be deleted. Further, for the purpose of modification of the functions of the promoter and the translation initiation site, e.g., for increase in expressivity, a fragment wherein the DNA base sequence of a region containing the promoter and the translation initiation site is modified can be conveniently used. Furthermore, it is possible to use a fragment wherein a DNA base sequence of a region having no relation to the functions of the promoter and the translation initiation site is modified.

The expression of the objective gene by using the promoter and the translation initiation site of the present invention can be carried out by preparing a fusin gene so that the frame of GLD gene coincides with that of the objective gene. Examples of the objective gene include genes coding for enzymes responsible for cephalosporin synthesis systems (e.g., isopenicillin N synthetase, isopenicillin N isomerase, deacetoxycephalosporin C synthetase (expandase), deacetoxycephalosporin C hydroxylase, deacetylcephalosporin C acetyltransferase, cephalosporin C acetylhydrase, etc.). Examples of the cephalosporins include isopenicillin N, penicillin N, deacetoxycephalosporin C, deacetylcephalosporin C, cephalosporin C and the like. The position of fusion of both genes is not specifically limited in so far as the fusion gene product has the desired activity. For example, the objective gene may be ligated so as to be expressed as fusion protein just behind an amino acid codon apart from the initiation codon of GLD gene, or just behind the initiation codon, directly.

The gene to be used for the expression may be any of genes isolated from chromosomes, complementary DNAs obtained from mRNAs, chemical synthetic genes, semisynthetic genes and the like. Preferably, those in which DNA base sequences are clarified are used. When a gene fused with GLD gene is prepared, DNA corresponding to a part of amino acids from the amino group terminal end can be removed in so far as the fusion gene product maintains its activity.

The fundamental operations for fusion of both genes are known and described in detail in literatures (see Methods in Enzymology, Vol. 68, 1979; Molecular Cloning, 1982). Further, in ligation of both genes, a synthetic DNA can be used as an adaptor between both genes. As the synthetic DNA, any DNA can be used in so far as the frames of both genes coincide with each other and the activity of the resulting objective gene is not lost. For example, a synthetic double stranded DNA from Sau3AI site located in upstream from the initiation codon of GLD gene to a suitable restriction enzyme site located in downstream from the initiation codon of the objective gene including the initiation codon of GLD gene can be used as the adaptor DNA. A general structure thereof is shown in FIG. 1.

As a host for introducing the above-prepared objective gene which is ligated by fusion in downstream from the region coding for the promoter and translation initiation site of GLD gene into *Acremonium chrysogenum*, any strain belonging to *Acremonium chrysogenum* can be used. For example, there can be used *Acremonium chrysogenum* ATCC 11550 strain, *Acremonium chrysogenum* ATCC 14553 strain, *Acremonium chrysogenum* N2 strain, mutants derived therefrom and the like. The above *Acremonium chrysogenum* N2 strain has been deposited at the Institute for Fermentation, Osaka (IFO, 17-85, Juso-honmachi 2-chome, Yodogawa-ku, Osaka-shi, Osaka-fu, Japan) under the accession number of IFO 32177 since Dec. 14, 1988. Further, it has been deposited at the Fermentation Research Institute, Agency of Industrial Science and Technology (FRI, 1-3, Higashi 1-chome, Tsukubashi, Ibaraki-ken, Japan) under Budapest treaty under the accession number of FERM BP-2204 since Dec. 23, 1988.

The ATCC numbers used herein represent the accession numbers at American Type Culture Collection (ATCC, 12301 Parklawn Drive, Rockville, Md. 20852, U.S.A.).

As a transformation method for introducing a gene into *Acremonium chrysogenum*, there can be employed a transformation of protoplasts [see S. W. Queener et al., Microbiology—1985, American Society for Microbiology, p 468 (1985)]. Further, in order to isolate transformants efficiently, after introducing the fusion gene into a plasmid having a suitable selective marker which functions in *Acremonium chrysogenum*, the plasmid is used for transformation of *Acremonium chrysogenum*. As the selective marker, there can be used any marker which can selectively separate a transformant. For example, GLD-hygromycin B resistant gene contained in plasmid pGH 21 (FIG. 15) can be used.

For culturing the transformant being capable of producing a cephalosporin of the present invention, there can be used culture media containing carbon sources, nitorgen sources and the like which are assimilable by the transformant. As the carbon sources, any assimilable ones can be used. Examples thereof include, in addition to glucose, sucrose, starch, soluble starch, glycerin and n-paraffin, organic acids such as acetic acid, fumaric acid, benzoic acid and the like, alcohols such as ethanol, butanol and the like, fats and oils (e.g., soybean oil, lard, etc.) and the like. They can be used alone or in combination thereof. As the nitrogen sources, there are, for example, peptone, soybean oil, meat extract, cottonseed meal, dry yeast, yeast extract, corn steep liquor, proflo, corn gluten meal, urea, ammonium salts (e.g., ammonium chloride), nitrates (e.g., potassium nitrate), other organic or inorganic nitorgenous substances (e.g., NZ amine (A), ammonium sulfate) and the like. They can be used alone or in combination thereof. As inorganic salts used as other components of the medium, there are, for example, various phosphates (e.g., potassium phosphate), sulfates (e.g., sodium sulfate), chlorides (e.g., magnesium chloride) and the like. Addition of respective ions of iron, magnesium, calcium, manganese, cobalt and the like has close relation to growth of the microorganism, production of a cephalosporin antibiotic, their stability and the like. These components of the medium can be suitably combined or selected according to a particular strain to be used, cultivation conditions and the like.

Although cultivation conditions such as a cultivation temperature, a cultivation period, a pH of a medium, aeration and the like are varied according to a particular strain to be used, a medium composition and the like, they can be selected and adjusted so that the accumulation of the desired cephalosporin becomes maximum. In many cases, the accumulation of cephalosporin in a culture broth becomes maximum by carrying out the cultivation under aerobic conditions at a cultivation temperature of 20° to 30° C. for a cultivation period of 4 to 14 days at a pH of a medium of 5.0 to 9.0.

A cephalosporin is produced and accumulated in a culture broth resulted from the cultivation. Since almost all the cephalosporins are present in a filtrate of a culture broth, they are preferably obtained from a liquid part resulted from removal of microbial cells from the culture broth by centrifugation or filtration. In order to separate and collect the cephalosporin, there can be employed known methods, for example, general methods for separation and collection of weak acidic organic substances. That is, the objective product can be advantageously collected by chromatography using an ion exchange resin (e.g., Amberlite IRA-900), activated charcoal, cellulose, silica gel or the like alone or in combination with gel filtration or the like. For determination of the cephalosporin, after separation of each components by thin layer chromatography, there can be employed a method for measuring antibacterial activity against bacteria to be tested or a method using cephalosporinase described in Nature, Vol. 246, p 154 (1973). Further, for identification of the cephalosporin, there can be employed elemental analysis, NMR spectra, filter paper electrophoresis, thin layer chromatography and the like.

The following Examples further illustrate the present invention in detail but are not to be construed to limit the scope thereof.

In Examples, all the percents are by weight unless otherwise stated.

EXAMPLE 1

Cloning of GLD gene of *Saccharomyces cerevisiae*

1) Preparation of chromosomal DNA of *Saccharomyces cerevisiae*

Frozen stock cells of *Saccharomyces cerevisiae* IFO 10147 was inoculated in 1 liter of YPD medium (yeast extract 10 g/liter, polypeptone 20 g/liter, glucose 20 g/liter) and incubated on a rotary shaking apparatus (200 rpm) at 30° C. for 18 hours. After centrifugation at 5000 G for 5 minutes, the resulting microbial cells were treated with the method of D. R. Cryer et al. [see Method in Cell Biology, XII, 39 (1975)] to obtain about 5 mg of chromosomal DNA.

2) Preparation of GLD gene detective probe

According to the report by J. P. Holland [see J. Biol. Chem., 254, 9839 (1979)], the DNA oligomer shown in FIG. 2 was prepared.

3) Preparation of gene library of *Saccharomyces cerevisiae*

The chromosomal DNA (30 μg) obtained in the above 1) was partially cleaved with the restriction enzyme MboI (5.4 units) at 37° C. for 20 minutes and, then, treated with a DNA polymerase I large fragment (manufactured by Takara Shuzo Co., Ltd., Japan) in the presence of dATP and dGTP. This was ligated with a XhoI cleaved fragment of phage vector λFix, partial fill-in arm (manufactured by STRATAGENE Cloning System Company, U.S.A.) by using T4 DNA ligase. This ligation reaction mixture was subjected to in vitro packaging by using Gigapack gold (manufactured by STRATAGENE Cloning System Company, U.S.A.). The titer of the gene library thus prepared was determined by using *Escherichia coli* LE 392 as an indicator bacterium. As the result, the titer was $1.0 \times 10^6$ pfu/ml.

4) Screening of GLD gene from gene library

After dilution of the gene library prepared in the above 3) in such a degree that 6000 plaques were appeared per one plate, plaques were formed on a plate by using *Escherichia coli* LE 392 as an indicator bacterium. According to the method described in pages 320 to 321 of the above "Molecular Cloning", plaques were lifted from the plate to a nitrocellulose filter. According to the method described in page 396 of the above "Molecular Cloning", the 5'-terminal of the DNA oligomer of FIG. 1 was labeled with the radioactive isotope $^{32}P$ by using T4 polynucleotide kinase and [γ-$^{32}P$]ATP. By using this as a probe, plaque hybridization was carried out (see pages 326 to 328 of the above "Molecular Cloning"). According to the method described in pages 371 to 372 of the above "Molecular Cloning", λDNA was separated from a positive plaque wherein hybridization with the probe was observed. λDNA thus obtained was cleaved with the restriction enzyme HindIII and, then, subjected to electrophoresis on an agarose gel (0.8%). According to Southern method (see pages 382 to 386 of the above "Molecular Cloning"), DNA was transferred to a nitrocellulose filter from the gel subjected to this electrophoresis. Southern hybridization between $^{32}P$ labeled DNA oligomer of FIG. 1 and the above DNA bonded nitrocellulose filter was carried out (see pages 387 to 389 of the above "Molecular Cloning"). As the result, hybridization with a HindIII fragment (2.3 kbp) was observed.

5) Subcloning of GLD gene

After cleaving the λDNA obtained in the above 4) with the restriction enzyme HindIII, the HindIII fragment (2.3 kbp) was isolated by electrophoresis on an agarose gel (1.0%) (see the above "Molecular Cloning", pages 150 to 162) and electro-elution (see Y. Takagi, "Gene Manipulation Manual", page 33, Kodan-sha Scientific, 1982). On the other hand, the vector plasmid pUC 18 was cleaved with the restriction enzyme HindIII. The two DNA fragments thus prepared were mixed and subjected to a ligation reaction with T4 DNA ligase. By using this ligation reaction mixture, *Escherichia coli* JM 109 strain was transformed to obtain a plasmid pGLD 19 wherein the HindIII fragment (2.3 kbp) containing GLD gene of *Saccharomyces cerevisiae* was inserted at HindIII site of pUC 18 (see FIG. 3).

EXAMPLE 2

Cloning of GLD gene of *Acremonium chrysogenum*

1) Preparation of chromosomal DNA of *Acremonium chrysogenum*

Frozen stock cells of *Acremonium chrysogenum* ATCC 11550 were inoculated in a culture medium (pH 7.0) containing sucrose (30 g/liter), meat extract (15 g/liter), corn steep liquor (5 g/liter) and CaCO$_3$ (1.5 g/liter) and incubated on a rotary shaking apparatus (200 rpm) at 28° C. for 48 hours. The culture broth (1 liter) was filtered off and the cells thus separated were treated according to the method of P. F. Hamlyn et al. [see Enzyme Microbiological Technology, 3, 321 (1981)] to prepare protoplasts. The resulting protoplasts were further treated according to the method of D. R. Cryer et al. [see Method in Cell Biology, XII, 39 (1975)] to obtain about 5 mg of a chromosomal DNA.

2) Preparation of gene library of *Acremonium chrysogenum*

The chromosomal DNA obtained in the above 1) (30 μg) was partially cleaved with the restriction enzyme MboI at 37° C. for 20 minutes and treated with a DNA polymerase I large fragment (manufactured by Takara Shuzo Co., Ltd., Japan) in the presence of dATP and dGTP. This was ligated with a XhoI cleaved fragment of phage vector λFix, partial fill-in arm (manufactured by STRATAGENE Cloning System Company, U.S.A.) by using T4 DNA ligase. This ligation reaction mixture was subjected to in vitro packaging by using Gigapack gold (manufactured by STRATAGENE Cloning System Company, U.S.A.). A titer of the gene library thus prepared was determined by using *Escherichia coli* LE 392 as an indicator bacterium. As the result, it was $6.5 \times 10^6$ pfu/ml.

3) Screening of GLD gene from gene library

After dilution of the gene library prepared in the above 2) in such a degree that 6000 plaques were appeared per one plate, plaques were formed on a plate by using *Escherichia coli* LE 392 as an indicator bacterium. According to the method described in page 320 to 321 of the above "Molecular Cloning", the plaques were lifted from the plate onto a nitrocellulose filter. Plaque hybridization (see pages 326 to 328 of the above "Molecular Cloning") was carried out at 42° C. for 16 hours in a hybridization solution containing 30% of formamide, 0.75M of sodium chloride, 0.075M of sodium citrate, 0.5% of sodium dodecylsulfate, 50 mM of Tris-HCl buffer (pH 7.5) and 100 μg/ml of heat denatured salmon sperm DNA by using the HindIII fragment (2.3 kbp) containing GLD gene of *Saccharomyces cerevisiae* of plasmid pGLD 19 labeled with the radioactive isotope $^{32}P$, according to nick translation method (see page 109 to 112 of the above "Molecular Cloning"), as a probe.

According to the method described in pages 371 to 372 of the above "Molecular Cloning", λDNA was isolated from a positive plaque wherein hybridization with the probe was observed. The resulting λDNA was cleaved with the restriction enzyme BamHI and, then, subjected to electrophoresis on an agarose gel (0.8%). According to Southern method (see pages 382 to 386 of the above "Molecular Cloning"), DNA was transferred from the gel subjected to electrophoresis to a nitrocellulose filter. Southern hybridization between the HindIII fragment (2.3 kbp) containing GLD gene of *Saccharomyces cerevisiae* of plasmid pGLD 19 labeled with the radioactive isotope $^{32}P$ and the above DNA bonded nitrocellulose filter was carried out at 42° C. for 16 hours in a hybridization solution containing 30% of formamide, 0.75 M of sodium chloride, 0.075 M of sodium citrate, 0.5% of sodium dodecylsulfate, 50 mM of Tris-HCl buffer (pH 7.5) and 100 μg/ml of heat denatured salmon sperm DNA.

As the result, hybridization with the BamHI fragment (4.5 kbp) was observed.

4) Subcloning of GLD gene

Figure 4:
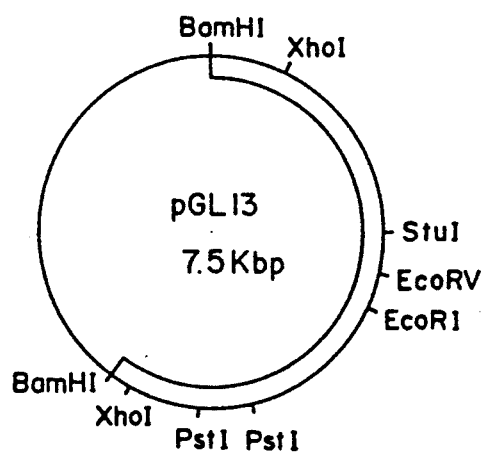
FIG. 4 is the restriction map of the plasmid pGL 13 obtained in Example 2-4) hereinafter.
Figure 7:
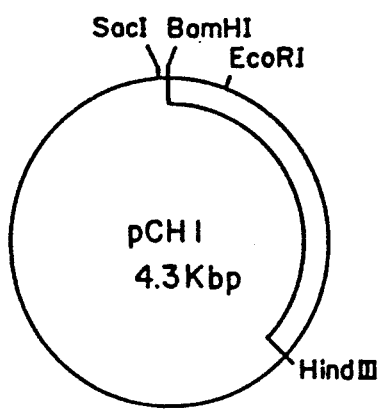
FIG. 7 is the restriction map of the plasmid pCH 1 obtained in Example 4 hereinafter.

After cleavage of λDNA obtained in the above 3) with the restriction enzyme BamHI, the BamHI fragment (4.5 kbp) was isolated by electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982). On the other hand, a vector plasmid pbluescript SK+ was cleaved with the restriction enzyme BamHI. Two DNA fragments thus obtained were mixed and subjected to a ligation reaction with T4 DNA ligase. *Escherichia coli* JM 109 strain was transformed with the ligation reaction mixture to obtain a plasmid pGL 13 (see FIG. 4) wherein the BamHI fragment (4.5 kbp) containing GLD gene of *Acremonium chrysogenum* was inserted at BamHI site of pbluescript SK+.

EXAMPLE 3

DNA base sequence of GLD gene

According to dideoxy synthetic chain termination method (see Eiichi Soeda et al., "Method for Determination of Base Sequence of Nucleic Acids", pages 61 to 113, Gakkai Shuppan Center, 1985), the DNA base sequence of PstI-XhoI fragment of pGL 13 (about 3.2 kbp) containing the GLD gene of *Acremonium chrysogenum* was determined. The result is shown in FIG. 5. The amino acid sequence of GLD presumed by the DNA base sequence thus determined is shown in FIG. 6.

EXAMPLE 4

Expression of hygromycin B phosphotransferase gene by utilizing promoter and translation initiation site of GLD gene 1) Preparation of plasmid pCH 1

According to the method of Kaster et al. [see Current Genetics, 8, 353 (1984)], a plasmid pCH 1 wherein the promoter and the DNA coding 3 amino acids from the amino-terminal end of hygromycin B phosphotransferase gene were deleted was prepared from a plasmid pGL 62 containing hygromycin B phosphotransferase gene [see L. Gritz et al., Gene, 25, 179 (1983)].

Figure 8:
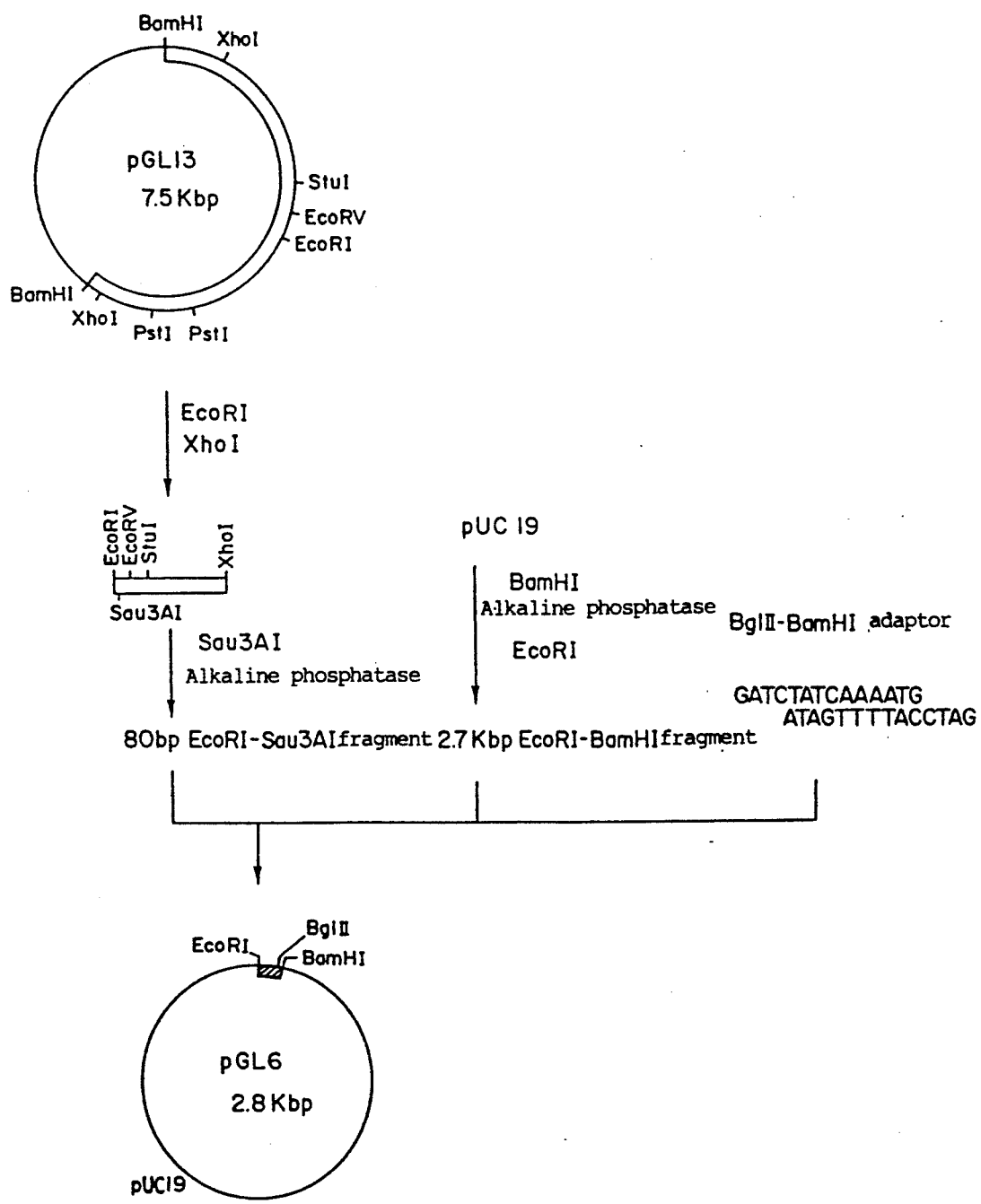
FIG. 8 illustrates the preparation of the plasmid pGL 6.

2) Preparation of plasmid pGL 6 (see FIG. 8)

A plasmid pGL 13 was cleaved with EcoRI and XhoI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a EcoRI-XhoI fragment (2.0 kbp). It was further cleaved with Sau3AI and, then, treated with alkaline phosphatase (manufactured by Takara Shuzo Co., Ltd., Japan). After electrophoresis on a polyacrylamide gel (10%), an EcoRI-Sau3AI fragment (about 80 bp) was isolated according to the method described in page 173 of the above "Molecular Cloning".

On the other hand, 5'-terminal ends of two 14 mer synthetic oligonucleotides (5'-GATCTATCAAAATG, 5'-GATCCATTTTGATA) were phosphorylated with T4 polynucleotide kinase (manufactured by Takara Shuzo Co., Ltd.), respectively, and, then, they were subjected to annealing to prepare a BglII-BamHI adaptor (see FIG. 8).

Then, a vector plasmid pUC 19 was cleaved with BamHI and treated with alkaline phosphatase (manufactured by Takara Shuzo Co., Ltd., Japan). It was further cleaved with EcoRI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate an EcoRI-BamHI fragment (2.7 kbp).

The above EcoRI-Sau3AI fragment (about 80 bp), BglII-BamHI adaptor and EcoRI-BamHI fragment (2.7 kbp) were ligated by using T4 DNA ligase to prepare the plasmid pGL 6.

Figure 9:
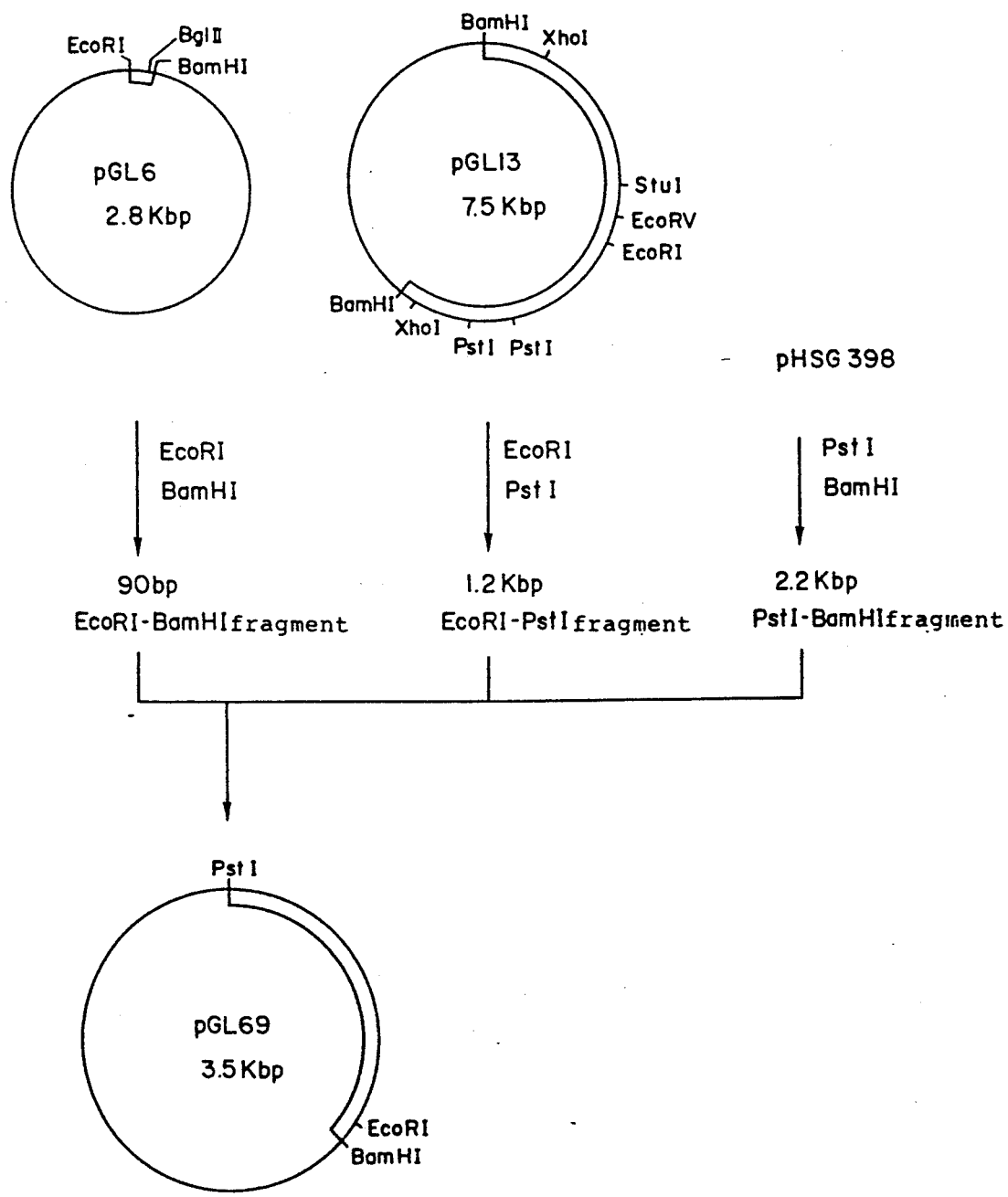
FIG. 9 illustrates the preparation of the plasmid pGL 69.

3) Preparation of plasmid pGL 69 (see FIG. 9)

The above plasmid pGL 6 was cleaved with EcoRI and BamHI and subjected to electrophoresis on a polyacrylamide gel (10%). According to the method described in page 173 of the above "Molecular Cloning", an EcoRI-BamHI fragment (about 90 bp) was isolated.

On the other hand, the plasmid pGL 13 described in Example 2-4) was cleaved with EcoRI and PstI and subjected to electrophoresis on an agarose gel (1.0%) (see pages 150 to 162 of the above "Molecular Cloning") and electro-elution (see Y. Takagi, "Gene Manipulation Manual", Kodan-sha Scientific, 1982) to isolate an EcoRI-PstI fragment (1.2 kbp).

A vector plasmid pHSG 398 (manufactured by Takara Shuzo Co., Ltd., Japan) was cleaved with PstI and BamHI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a PstI-BamHI fragment (2.2 kbp).

The above EcoRI-BamHI fragment (about 90 bp), EcoRI-PstI fragment (1.2 kbp) and PstI-BamHI fragment (2.2 kbp) were ligated by using T4 DNA ligase to prepare the plasmid pGL 69.

Figure 10:
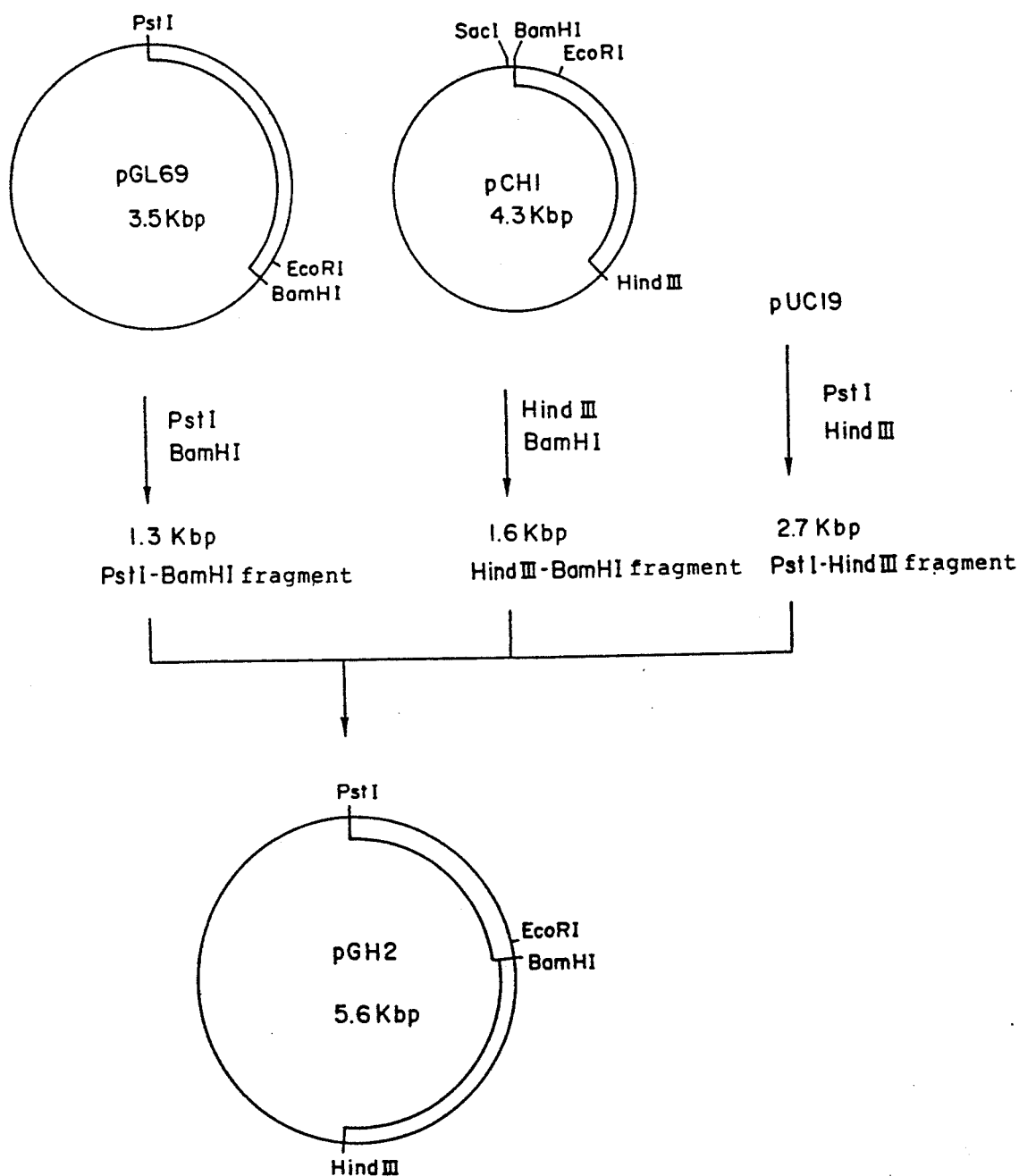
FIG. 10 illustrates the preparation of the plasmid pGL 2.

4) Preparation of plasmid pGH 2 (see FIG. 10)

The above plasmid pGL 69 was cleaved with PstI and BamHI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a PstI-BamHI fragment (1.3 kbp).

The plasmid pCH 1 described in the above 1) was cleaved with HindIII and BamHI and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a HindIII-BamHI fragment (1.6 kbp).

The vector plasmid pUC 19 was cleaved with PstI and HindIII and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a PstI-HindIII fragment (2.7 kbp).

The above PstI-BamHI fragment (1.3 kbp), HindIII-BamHI fragment (1.6 kbp) and PstI-HindIII fragment (2.7 kbp) were ligated by using T4 DNA ligase to prepare the plasmid pGH 2.

5) Preparation of protoplasts from

Acremonium chrysogenum ATCC 11550 strain

Frozen stock of conidia of Acremonium chrysogenum ATCC 11550 strain (1×10⁹ conidia) were inoculated in a culture broth (pH 7.0) containing sucrose (30 g/liter), meat extract (15 g/liter) and corn steep liquor (5 g/liter) and incubated on a rotary shaking apparatus (200 rpm) at 28° C. for 18 hours. After filtering off the culture broth (250 ml), the resulting cells were washed with sterilized water, suspended in McIlvaine buffer (30 ml) (13.5mM citric acid-174 mM sodium phosphate, pH 7.3) containing 0.01 M dithiothreitol and gently shaken at 28° C. for 1 hour. The cells were filtered off, washed and suspended in McIlvaine buffer (60 ml) containing Zymolyase 20T (3 mg/ml) (manufactured by Seikagaku Kogyo, Co., Ltd., Japan), Lytic enzyme LI (3 mg/ml) (manufactured by BDH Chemicals Corp., U.S.A.) and 0.7 M NaCl. The cell suspension was gently shaken at 30° C. for 3 hours and then hyphae and protoplasts were separated by a glass filter (G-1, manufactured by Iwaki Glass Co., Ltd., Japan). The filtrate was centrifuged (1000 G, for 5 minutes) to precipitate protoplasts. The protoplasts were washed twice with 0.7 M NaCl and suspended in 0.7 M NaCl so that the concentration of the protoplasts became 5×10⁸ protoplasts/ml.

6) Transformation of protoplast by pGH 2

The plasmid pGH 2 (10 μg, 5 μl) was added to the protoplast suspension (0.1 ml) and the mixture was briefly mixed. Then, to the mixture were added 0.7 M NaCl (0.4 ml), PEG 4000 (36%) (Wako Pure Chemical Industries, Ltd., Japan) and 0.05 M glycine buffer (0.5 ml, pH 7.5) containing 106 mM $CaCl_2$ and the mixture was lightly mixed. After standing at room temperature for 10 minutes, 0.7 M NaCl (5 ml) was added and the mixture was centrifuged (1000 G, for 5 minutes). The precipitated protoplasts was re-suspended in 0.7 M NaCl (1 ml). This transformed protoplast suspension (0.1 ml) was spread on a plate containing a protoplast regeneration medium [30 ml, trypticase soy agar (BBL Microbiology systems, manufactured by Becton Dexon and Company, U.S.A.) containing 10.3% sucrose]and incubated at 15° C. for 20 hours. Then, the protoplast regeneration medium (5 ml, warmed to 45° C.) containing hygromycin B (350 μg/ml) was overlaid thereon and the incubation was carried out at 25° C. for 6 to 12 days to select hygromycin B resistant transformants. From 1 ml of the transformed protoplast suspension, 10 hygromycin B resistant transformants were obtained.

7) Analysis of hygromycin B resistant transformant by Southern hybridization

According to the same manner as described in Example 2-1), the DNA were separated from a hygromycin B resistant transformants. The DNA was subjected to electrophoresis on an agarose gel (0.8%) (see pages 150 to 162 of the above "Molecular Cloning") and, according to Southern method (see pages 382 to 386 of the above "Molecular Cloning"), the DNA were transferred from the gel subjected to electrophoresis to a nitrocellulose filter. According to nick translation method (see pages 109 to 112 of the above "Molecular Cloning"), Southern hybridization (see pages 387 to 389 of the above "Molecular Cloning") between the BamHI-HindIII fragment containing the hygromycin B phosphotransferase gene of pCH 1 labeled with the radioactive isotope $^{32}P$ and the above DNA bonded nitrocellulose was carried out. Although no hybridization was observed for the DNA of *Acremonium chrysogenum* ATCC 11550, clear hybridization was observed for the DNA of the hygromycin B resistant transformant.

In view of the above facts of Example 4-5) and 6), it has been clear that the expression of hygromycin B phosphotransferase gene of pGH 2 was controlled by the promoter and translation initiation site of GLD gene in *Acremonium chrysogenum* cells.

EXAMPLE 5

Figure 11:
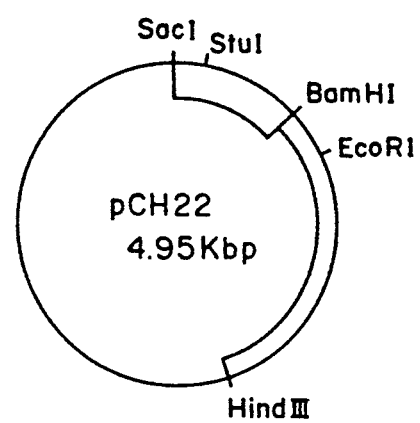
FIG. 11 is the restriction map of the plasmid pCH 22.

A) Comparision of expressivity of promoter and translation initiation site of GLD gene and that of promoter and translation initiation site of IPMDH gene According to the same manner as described in Example 4-5) and 6), Acremonium chrysogenum ATCC 11550 was subjected to protoplast transformation with the plasmid pCH 22 having hygromycin B phosphotransferase gene (see FIG. 11) which expression was controlled by the promoter and translation initiation site of β-isopropylmalate dehydrogenase gene (IPMDH gene) from *Acremonium chrysogenum*.

Then, the growth rate of the resulting hygromycin B resistant transformant was compared with that of the hygromycin B resistant transformant with pGH 2 obtained in Example 4—4) to 6). Namely, conidia were separated from the transformant with pCH 22 and that with pGH 2, respectively, and smeared on trypticase agar plates containing 50 μg/ml of hygromycin B. Formation of a colony (3 mm in diameter) by the transformant with pCH 22 took 10 days. To the contrary, formation of a colony (3 mm in diameter) by the transformant with pGH 2 took only 4 days.

Namely, the promoter and translation initiation site of GLD gene expresses hygromycin B phosphotransferase gene more potently than the promoter and translation initiation site of IPMDH gene.

Figure 18:
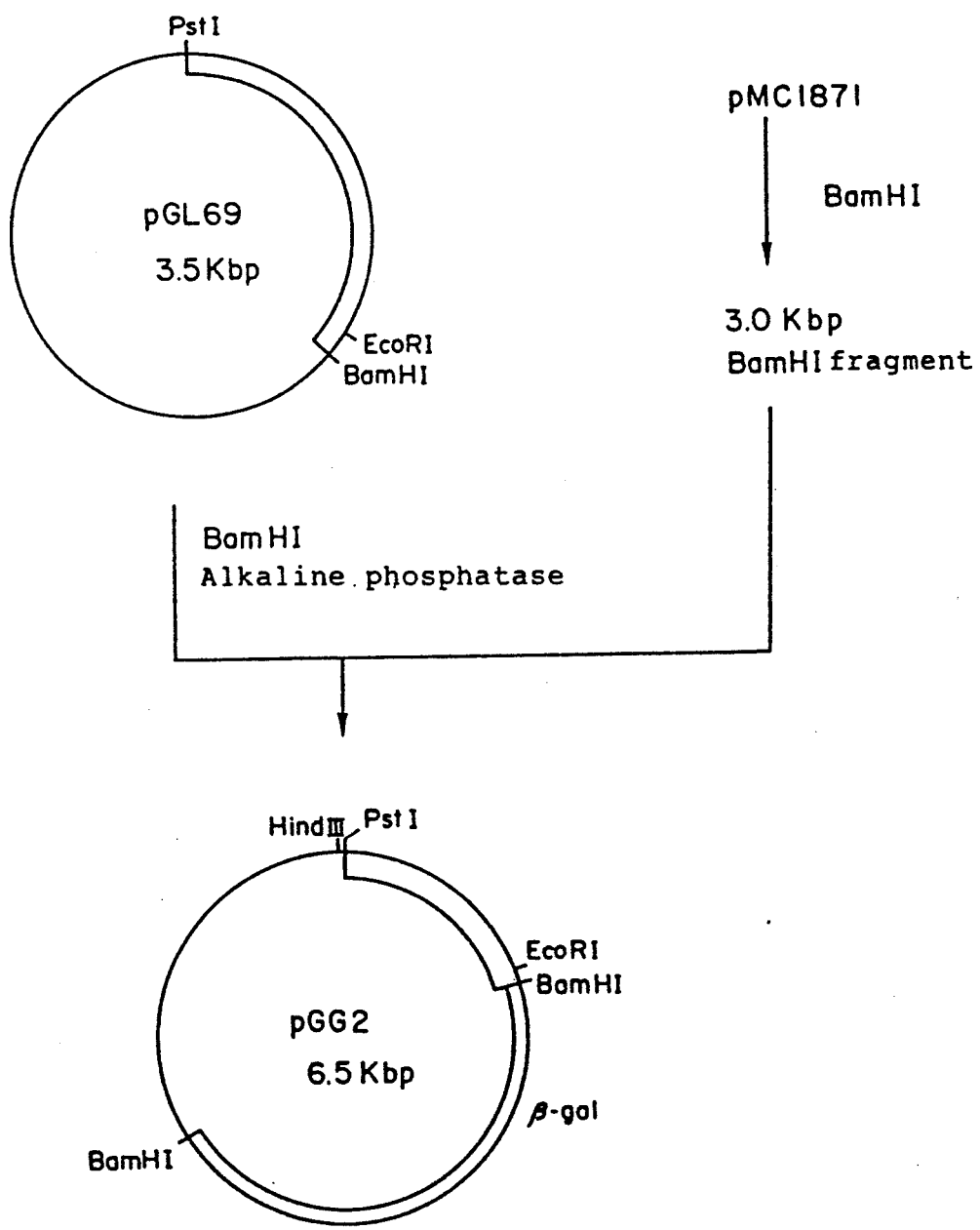
FIG. 18 illustrates the preparation of the plasmid pGG 2.
Figure 19:
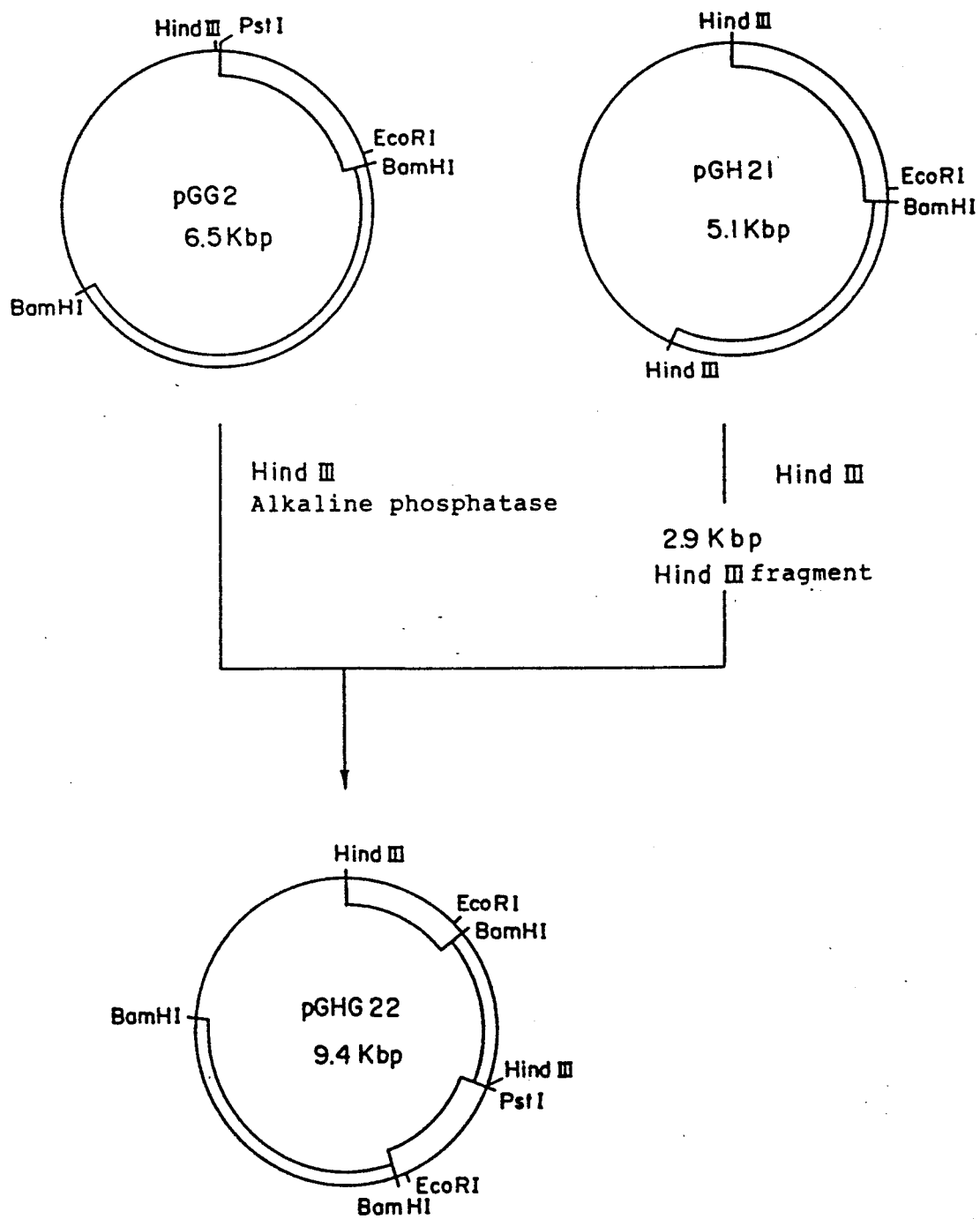
FIG. 19 illustrates the preparation of the plasmid pGHG 22.

B) Comparison of expressivities by using *Escherichia coli* β-galactosidase gene 1) Preparation of plasmid pGHG 22 (see FIGS. 18 and 19)

The plasmid pMC 1871 (manufactured by AB Pharmacia, Sweden) was cleaved with BamHI and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a BamHI fragment (3.0 kbp).

BamHI fragments of pGL 69 and pMC 1871 were ligated with T4 DNA ligase to prepare the plasmid pGG 2.

The above plasmid pGG 2 was cleaved with HindIII and treated with alkaline phosphatase (manufactured by Takara Shuzo Co., Ltd., Japan).

The plasmid pGH 21 described in Example 6-4) hereinafter was cleaved with HindIII and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a HindIII fragment (2.9 kbp).

The above HindIII fragment of pGG 2 and the HindIII fragment (2.9 kbp) were ligated with T4 DNA ligase to obtain the plasmid pGHG 22.

Figure 20:
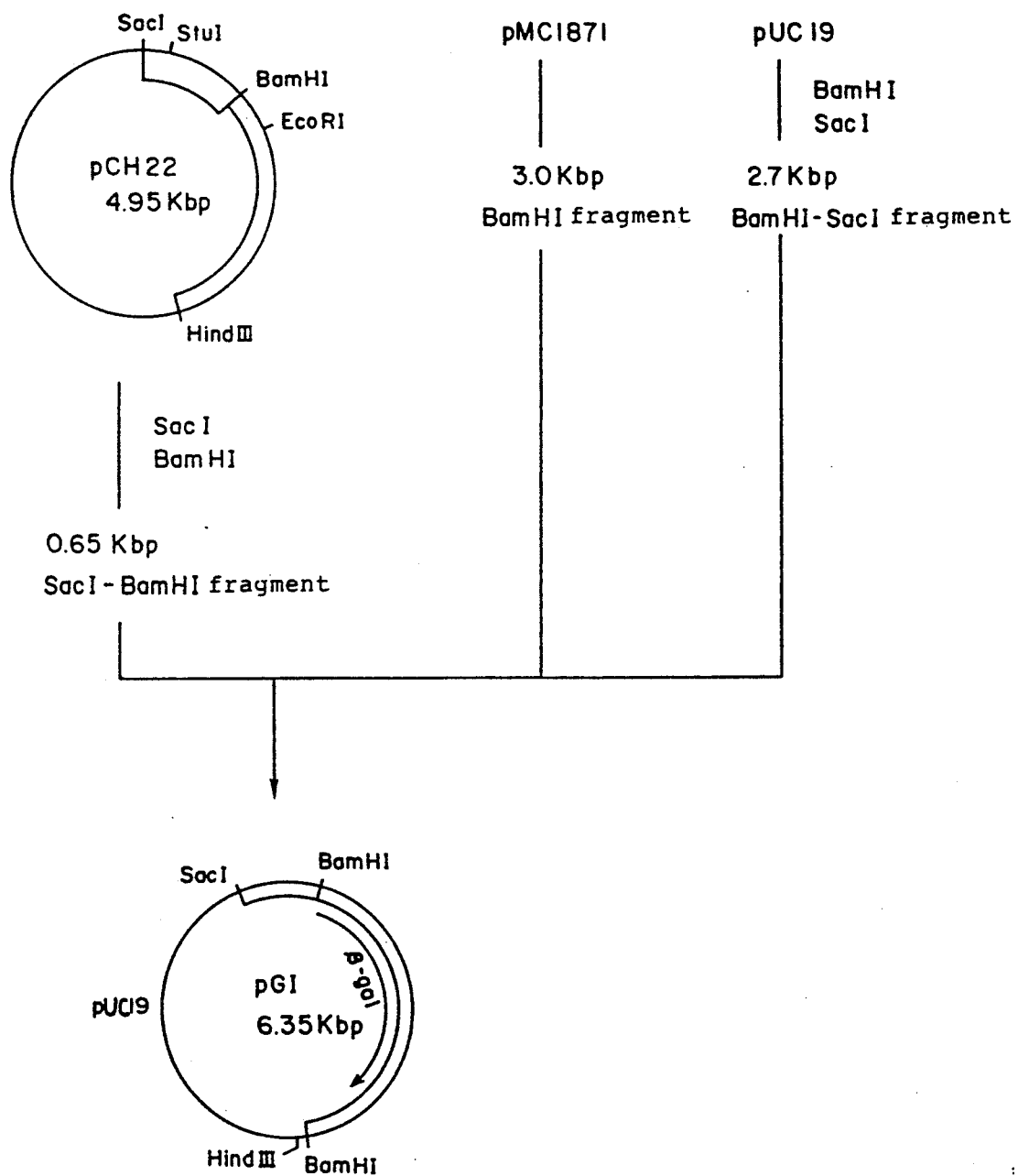
FIG. 20 illustrates the preparation of the plasmid pGI.
Figure 21:
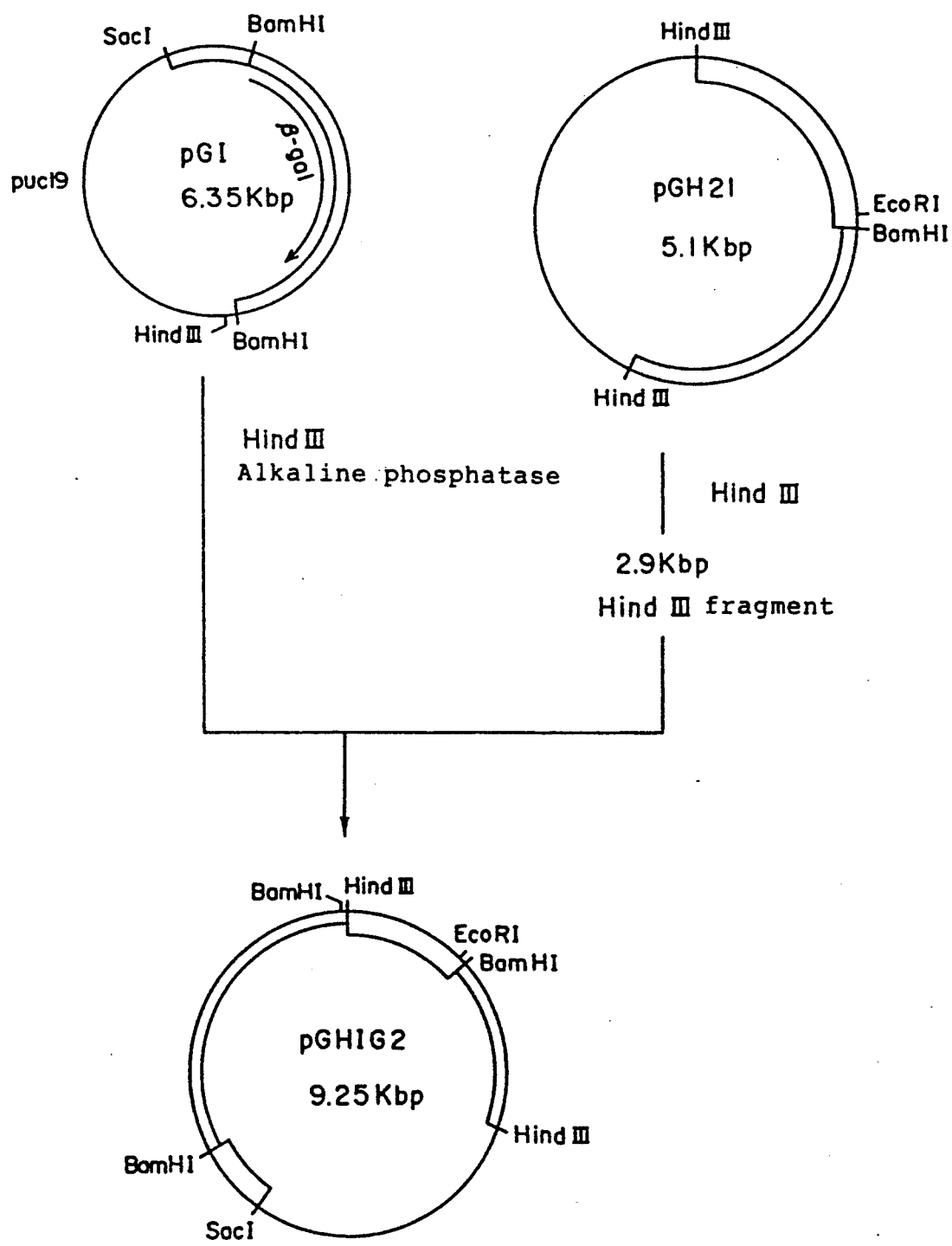
FIG. 21 illustrates the preparation of the plasmid pGHIG 2.

2) Preparation of plasmid pGHIG 2 (see FIGS. 20 and 21)

The plasmid pCH 22 described in Example 5-A) was cleaved with SacI and BamHI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a SacI-BamHI fragment (0.65 kbp).

The plasmid pMC 1871 (manufactured by AB Pharmacia, Sweden) containing β-galactosidase gene was cleaved with BamHI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a BamHI fragment (3.0 kbp).

The vector plasmid pUC 19 was cleaved with BamHI and SacI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a BamHI-SacI fragment (2.7 kbp).

These SacI-BamHI fragment (0.65 kbp), BamHI fragment (3.0 kbp) and BamHI-SacI fragment were ligated with T4 ligase to obtain the plasmid pG 1.

This plasmid pG 1 was cleaved with HindIII and treated with alkaline phosphatase (manufactured by Takara Shuzo Cp., Ltd., Japan).

HindIII fragment (2.9 kbp) of the plasmid pGH 21 described in Example 6-4) hereinafter was ligated with HindIII fragment of pG 1 with T4 ligase to prepare pGHIG 2.

3) Protoplast transformation with plasmids pGHG 22 and pGHIG 2

According to the same manner as described in Example 4–5) and 6), *Acremonium chrysogenum* ATCC 11550 was subjected to protoplast transformation by using plasmids pGHG 22 and pGHIG 2 to obtain 5 hygromycin B resistant transformants from the respective plasmids.

4) The hygromycin B resistant transformants obtained in the above 3) were inoculated in trypticase soy broth (BBL Microbiology systems, manufactured by Becton Dexon and Company, U.S.A.) containing 30 g/liter of sucrose and incubated on a rotary shaking apparatus (240 rpm) at 28° C. for 3 days. Culture broth (100 ml) was filtered off and the resulting cells were washed with 0.7% NaCl and suspended in 50 mM sodium phosphate butter (pH 7.0) containing EDTA (1 mM) and RMSF (20 μM). The cell suspension was ultrasonicated (160W, 5 minutes) and centrifuged at 20000 G for 15 minutes to obtain a crude enzyme solution. According to the method of J. H. Miller (see Experiment in Molecular Genetics, Cold Spring Habor Laboratory, published by Tokyo Daigaku Shuppan-kai, pages 352 to 355, 1972), β-galactosidase activity was determined. The results are shown in Table 1.

TABLE 1

| Strain | Plasmid | Number of strains | Enzymatic activity (average)* |
|---|---|---|---|
| ATCC 11550 | — | 5 | 85.9 |
| ATCC 11550 | pGHG 22 | 5 | 487.5 |
| ATCC 11550 | pGHIG 2 | 5 | 143.3 |

*units/mg · protein

Namely, the promoter and translation initiation site of GLD gene expresses β-galactosidase gene more potently than the promoter and translation initiation site of IPMDH gene.

EXAMPLE 6

Figure 12:
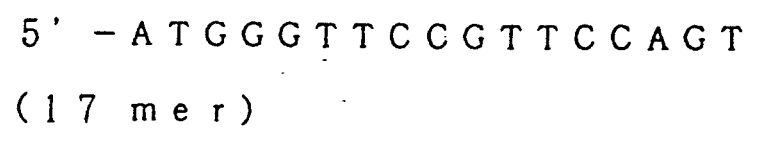

Expression of isopenicillin N synthetase gene by utilizing promoter and translation initiation site of GLD gene 1) Preparation of probe for detection of isopenicillin N synthetase gene According to the report of S. M. Samson et al. [Nature, 318, 191 (1985)], the DNA oligomer shown in FIG. 12 was prepared.

2) Cloning of isopenicillin N synthetase gene from gene library to *Escherichia coli*

Figure 13:
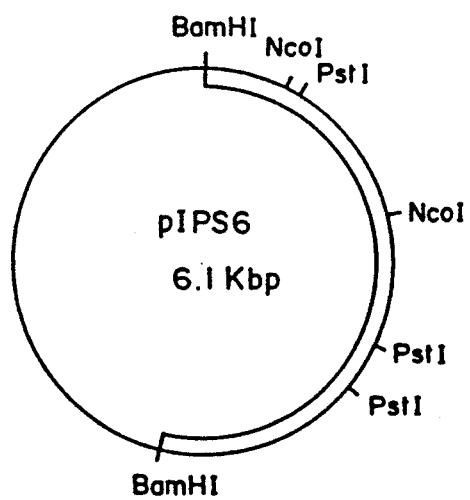
FIG. 13 is the restriction map of the plasmid pIPS 6 obtained in Example 6-2) hereinafter.

According to the same manner as described in Example 2—2), isopenicillin N synthetase gene was cloned and further subcloned to prepare the plasmid pIPS 6 (see FIG. 13) wherein BamHI fragment (3.1 kbp) containing isopenicillin N synthetase gene of *Acremonium chrysogenum* was inserted at BamHI site of the vector plasmid pUC 18.

Figure 14:
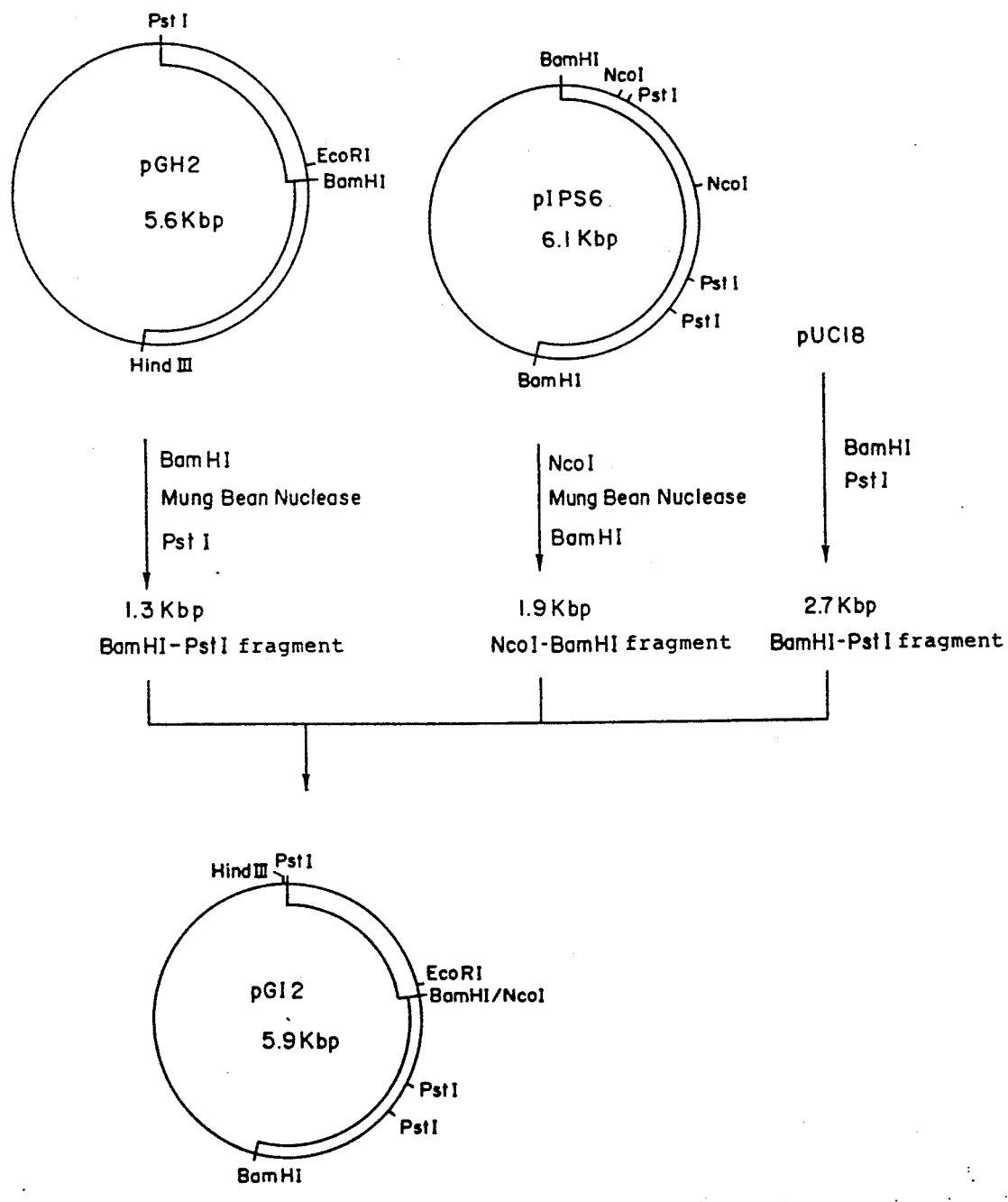
FIG. 14 illustrates the preparation of the plasmid pGI 2.

3) Preparation of pGI 2 (see FIG. 14)

The plasmid pGH 2 prepared in Example 4—4) was cleaved with BamHI and treated with Mung Bean nuclease (manufactured by Takara Shuzo Co., Ltd., Japan) to convert into the flush end. This was cleaved with PstI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a BamHI-PstI fragment (1.3 kbp).

The above-prepared plasmid pIPS 6 as cleaved with NcoI and treated with Mung Bean nuclease (manufactured by Takara Shuzo Co. Ltd., Japan) to convert into the flush end. This was cleaved with BamHI and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a NcoI-BamHI fragment (1.9 kbp).

The vector plasmid pUC 18 was cleaved with BamHI and PstI and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a BamHI-PstI fragment (2.7 kbp). These BamHI-PstI fragment (1.3 kbp), NcoI-BamHI fragment (1.9 kbp) and BamHI-PstI fragment (2.7 kbp) were ligated with T4 ligase to prepare the plasmid pGI 2.

4) Preparation of pGH 21

The plasmid pGL 69 prepared in Example 4-3) was cleaved with BamHI and HindIII and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a BamHI-HindIII fragment (1.3 kbp).

The plasmid pCH 1 described in Example 4-1) was cleaved with HindIII and BamHI and subjected to electrophoresis on an agarose gel (1.0%) (see pages 150 to 162 of the above "Molecular Cloning") and electro-elution (see Y. Takagi, "Gene Manipulation Manual", page 33, Kodansha Scientific, 1982) to isolate a HindIII-BamHI fragment (1.6 kbp).

The vector plasmid pHSG 398 (manufactured by Takara Shuzo Co., ltd., Japan) was cleaved with HindIII and treated with alkaline phosphatase (manufactured by Takara Shuzo Co., Ltd., Japan).

Figure 15:
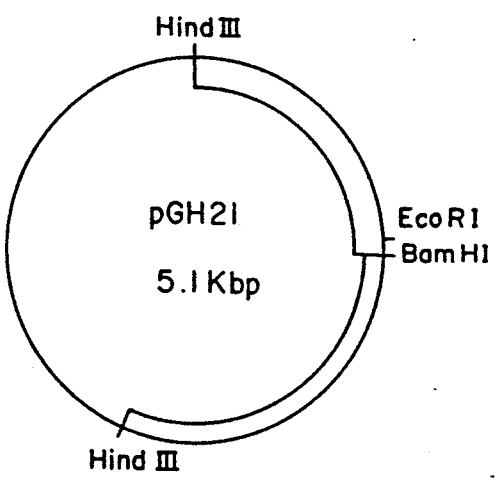
FIG. 15 is the restriction map of the plasmid pGH 21 obtained in Example 6-4) hereinafter.

These BamHI-HindIII fragment (1.3 kbp), HindIII-BamHI fragment (1.6 kbp) and HindIII fragment of pHSG 398 were ligated with T4 ligase to prepare the plasmid pGH 21 (see FIG. 15).

Figure 16:
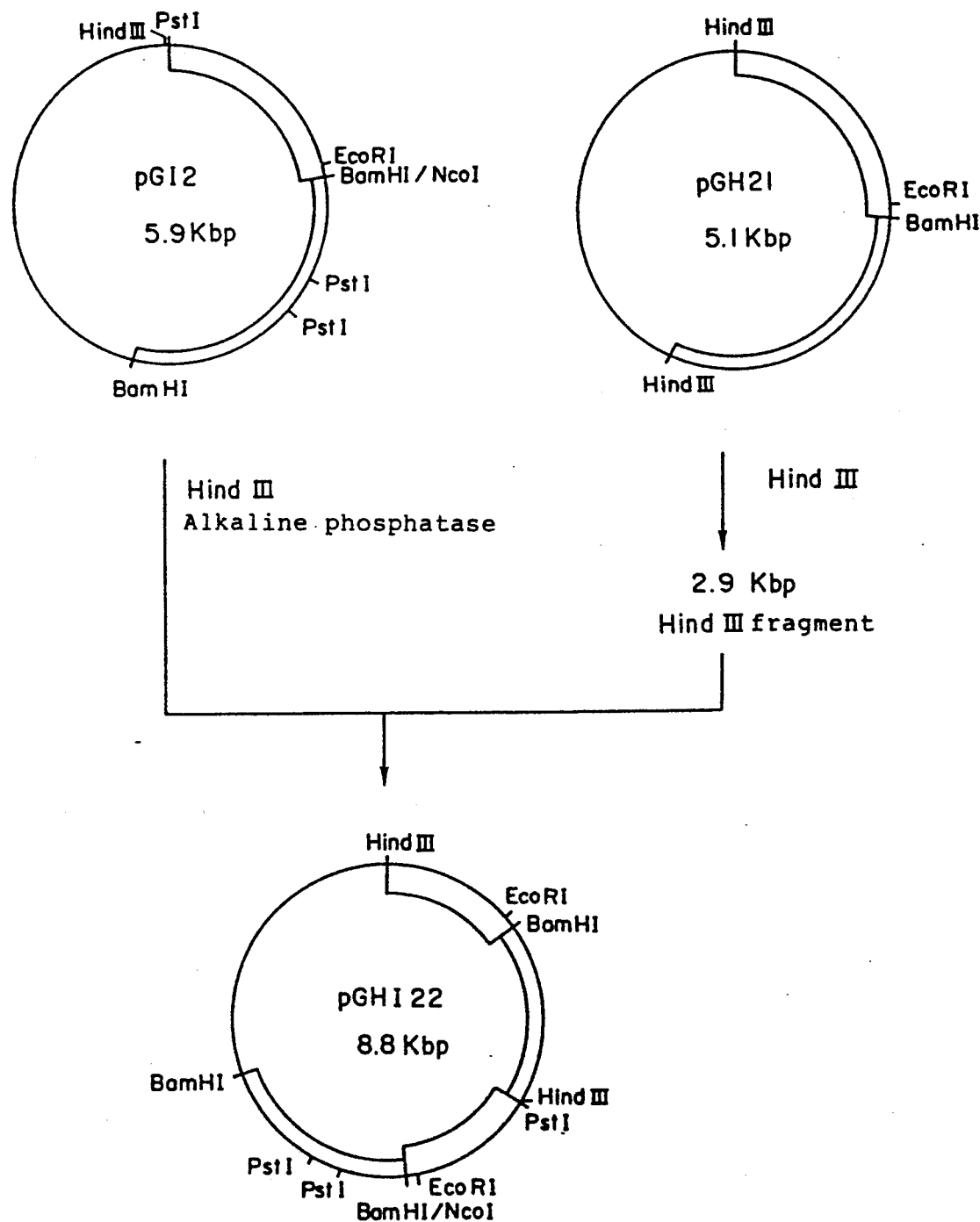
FIG. 16 is the restriction map of the plasmid pGHI 22.

5) Preparation of pGHI 22 (see FIG. 16)

The plasmid pGI 2 described in the above 3) was cleaved with HindIII and treated with alkaline phosphatase (manufactured by Takara Shuzo Co., ltd., Japan).

The above plasmid pGH 21 was cleaved with HindIII and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a HindIII fragment (2.9 kbp).

These HindIII fragment of pGI 2 and HindIII fragment (2.9 kbp) were ligated with T4 ligase to prepare the plasmid pGHI 22.

6) Protoplast transformation with plasmid pGHI 22

When Acremonium chrysogenum N2 strain (isopenicillin N synthetase gene defective strain) was subjected to protoplast transformation with the plasmid pGHI 22 according to the same manner as described in Example 4-5) and 6), 12 hygromycin B resistant transformants were obtained.

Figure 17:
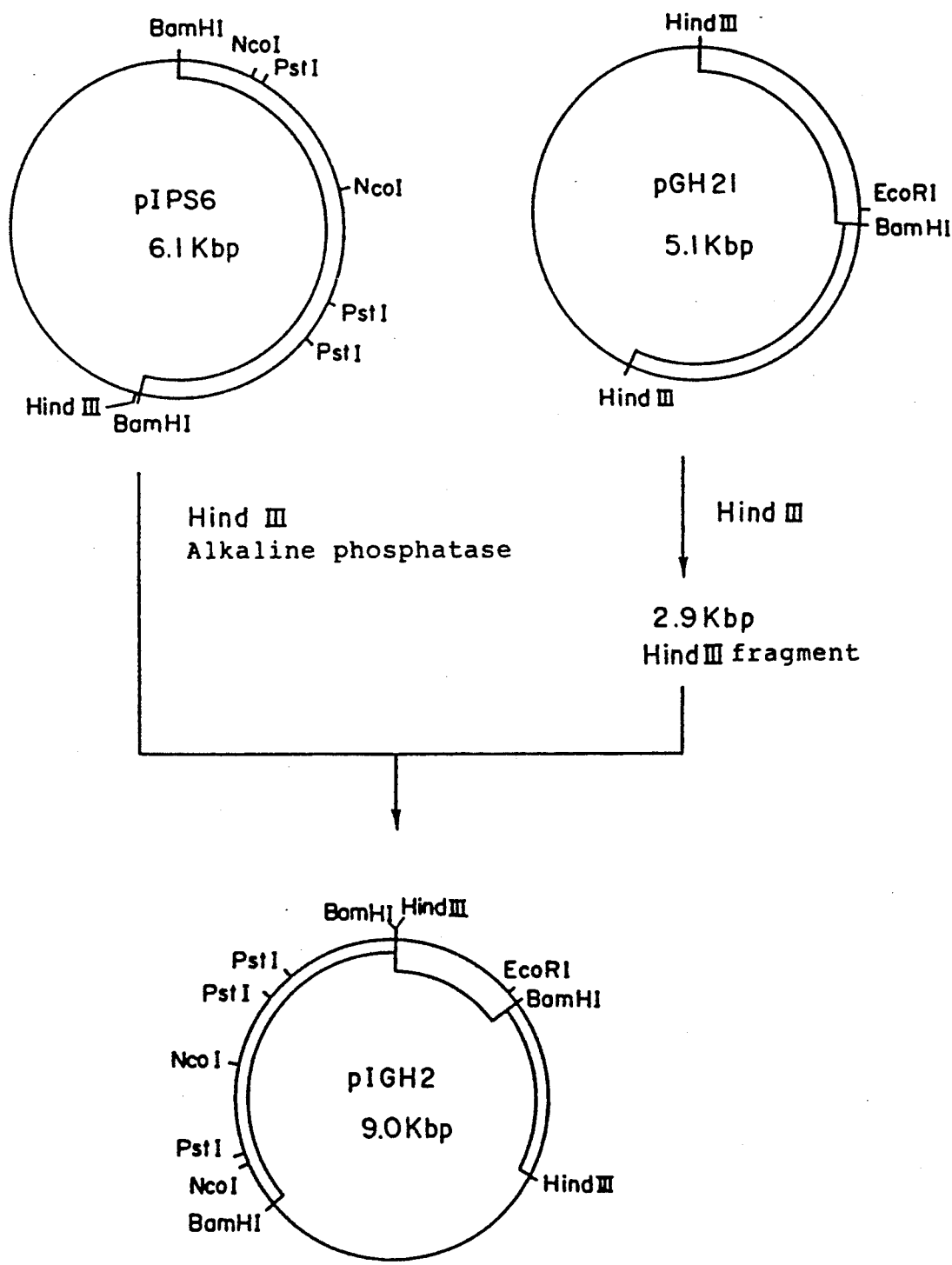
FIG. 17 illustrates the preparation of the plasmid pIGH 22.

7) Preparation of pIGH 2 (see FIG. 17)

The plasmid pIPS 6 described in the above 2) was cleaved with HindIII and treated with alkaline phosphatase (manufactured by Takara Shuzo Co., Ltd., Japan).

The above plasmid pGH 21 was cleaved with HindIII and subjected to electrophoresis on an agarose gel (1.0%) (see pages 150 to 162 of the above "Molecular Cloning") and electro-elution (see Y. Takagi, "Gene Manipulation Manual", page 33, Kodan-sha Scientific, 1982) to isolate a HindIII fragment (2.9 kbp).

These HindIII fragment of pIPS 6 and HindIII fragment (2.9 kbp) were ligated with T4 ligase to prepare the plasmid pIGH 2.

8) Protoplast transformation with plasmid pIGH 2

When Acremonium chrysogenum N2 strain (isopenicillin N synthetase gene defective strain) was subjected to protoplast transformation with the plasmid pIGH 2 according to the same manner as described in Example 4-5) and 6), 12 hygromycin B resistant transformants were obtained.

9) Cultivation of hygromycin B resistant transformants

The hygromycin B resistant transformants obtained in the above 6) and 8) were inoculated in SBF medium (sucrose 30 g/liter, DL-methionine 5 g/liter, soy bean flour 32 g/liter, corn steep liquor 0.5 g/liter, $CaCO_3$ 1.5 g/liter, pH 6.8) and incubated on a rotary shaking apparatus (240 rpm) at 28° C. for 5 days. Each culture broth was centrifuged at 10000 G for 10 minutes and the total cephalosporin concentration in the resulting supernatant was determined according to an enzymatic method (see Y. Fujisawa et al., Nature New Biology, 246, pp. 154–155. 1973). The results are shown in Table 2.

TABLE 2

| Plasmid | Number of strains | Yield (average)* |
|---|---|---|
| pGHI 22 | 12 | 428 |
| pIGH 2 | 12 | 338 |

*µg/ml

As seen from Table 2, in comparison with the hygromycin B resistant transformant with pIGH 2, that with pGHI 22 wherein the promoter and translation initiation site of isopenicillin N synthetase gene in pIGH 2 has been replaced with the promoter and translation initiation site of GLD gene shows higher yield.

As described hereinabove, the GLD gene promoter of the present invention can efficiently express foreign genes by using fungi (e.g., Acremonium chrysogenum) as hosts. Therefore, it can provide industrial advantages. For example, improvement in yield of an antibiotic (e.g., cephalosporin C, deacetylcephalosporin C, etc.) is expected.

What is claimed is:

1. A DNA fragment comprising the base sequence shown in FIG. 5.

2. A plasmid comprising a glyceraldehyde-3-phosphate dehydrogenase gene promoter obtained from the DNA fragment of claim 1.

3. The plasmid of claim 2, wherein a structural gene is downstream and operatively linked to the promoter.

4. The plasmid of claim 2, wherein a glyceraldehyde-3-phosphate dehydrogenase gene translation initiation site is downstream and operatively linked to the glyceraldehyde-3-phosphate dehydrogenase gene promoter site of Acremonium chrysogenum.

5. The plasmid of claim 4, wherein a structural gene is downstream and operatively linked to the promoter or the initiation site.

6. Acremonium chrysogenum transformed with the plasmid of claim 3.

7. Acremonium chrysogenum transformed with the plasmid of claim 5.

8. The transformant of claim 6 which is capable of producing a cephalosporin.

9. The transformant of claim 7 which is capable of producing a cephalosporin.

* * * * *